United States Patent [19]
Huth et al.

[11] Patent Number: 5,209,783
[45] Date of Patent: May 11, 1993

[54] METHOD FOR SIMULTANEOUSLY CLEANING, DECOLORIZING AND THERMALLY DISINFECTING CONTACT LENSES

[75] Inventors: Stanley W. Huth, Newport Beach; Sam W. Lam, Laguna Niguel; Abraham M. Espiritu, Oceanside, all of Calif.

[73] Assignee: Allergan, Inc., Irvine, Calif.

[21] Appl. No.: 816,860

[22] Filed: Jan. 3, 1992

Related U.S. Application Data

[63] Continuation of Ser. No. 633,596, Dec. 21, 1990, abandoned.

[51] Int. Cl.$^5$ .............................. B08B 3/10; B08B 7/00
[52] U.S. Cl. ........................................ 134/19; 134/42; 252/DIG. 12
[58] Field of Search ................................... 134/19, 42; 252/DIG. 12

[56] References Cited

U.S. PATENT DOCUMENTS

| Re. 32,672 | 5/1988 | Huth et al. | 252/174.12 |
|---|---|---|---|
| 4,285,738 | 8/1981 | Ogata | 134/26 |
| 4,614,549 | 9/1986 | Ogunbiyi et al. | 134/19 |
| 4,690,773 | 9/1987 | Ogunbiyi et al. | 252/DIG. 12 |
| 4,863,627 | 9/1989 | Davies et al. | 252/95 |

OTHER PUBLICATIONS

"Protein: A Sourse of Lense Discoloration", Ralph P. Stone, Mary F. Mowrey-McKee and Paul Kreutzer, Sep. 1984.

"Identification and Management of Soft Contact Lense Deposits" by Patrick J. Caroline, Ocular Therapy, 1985-vol. 2.

"Clinical Experiences with Chemical Va. Thermal Disinfection of Hydrophilic Lenses", by Gerald L. Feldman and William R. Bailey, Jr., Contact Lense Journal, Sep. 1974.

*Primary Examiner*—Theodore Morris
*Assistant Examiner*—Zeinab El-Arini
*Attorney, Agent, or Firm*—Spensley Horn Jubas & Lubitz

[57] ABSTRACT

A method for removing yellow contact lens discoloration involves immersing yellow colored contact lenses in a solution including a proteolytic enzyme and a reducing agent and then heating the solution for a time and at a temperature sufficient to remove substantially all yellow contact lens discoloration. The method also functions to simultaneously clean, disinfect and remove yellow discoloration from a contact lens. The lens is immersed in an aqueous solution including an effective amount of a thiol and an enzyme, and the solution is heated above ambient temperature for a time and at a temperature sufficient to remove substantially all yellow contact lens discoloration and contact lens protein accretions and to disinfect the lens. Preferably the solution is heated to a maximum temperature in a range of approximately 80° C. to approximately 90° C.

35 Claims, No Drawings

METHOD FOR SIMULTANEOUSLY CLEANING, DECOLORIZING AND THERMALLY DISINFECTING CONTACT LENSES

This is a continuation of application Ser. No. 07/633,596, filed Dec. 21, 1990, now abandoned.

BACKGROUND

This invention relates to a method and composition for preventing and removing contact lense discoloration. More specifically, this invention covers the simultaneous cleaning, decolorizing and thermally disinfecting of contact lenses by means of immersing the discolored lense in a solution containing a mixture of a reducing agent and an enzyme, and heating the solution.

RELATED ART

The growth of the contact lense industry has led to a dramatic increase in the number of lenses and care regimens in the marketplace. Designing care regimens to meet the needs of all possible permutations has become a challenge to the industry. In particular, a goal of the lense care industry is to simplify the lense care regimen to obtain greater patient compliance.

One area of interest is the impact of care regimens on lense discoloration. Discoloration limits the useful life of the lense and increases the risk of ocular response. Yellow, orange, amber, brown, gray and pink lense discolorations after use have been reported. It has been suggested that this phenomenon is most closely associated with high water content lenses.

Discoloration, in itself, is not believed to be a type of deposition; rather, it is believed to be an indication or sign of deposition. Discoloration has been attributed to a variety of sources: aging of the lense material, uptake of preservatives, uptake of colored metabolites, invasion of pigmented microorganisms, and the presence of foreign bodies of metallic origin.

Thermal disinfection of contact lenses is well known. See, for example, U.S. Pat. No. 4,614,549 to Ogunbiyi. However, some studies indicate that thermal disinfection of lenses having protein deposits is the key factor in lense discoloration, especially in high water content lenses. See Stone RP, Mowrey McKee MF and Krutzer, P, "Protein: A Source of Lense Discoloration", Contact Lens Forum, Sep., 1984 at pages 33–41. Some studies indicate that thermal disinfection should be avoided to minimize discoloration. See Caroline, PJ, "Identification and Management of Soft Contact Lens Deposits", Ocular Therapy, 1985, Volume 2 at pages 14-15. Likewise, chemical disinfection has been suggested to reduce the incidence of pigment deposits.

The evolution of contact lenses from glass to the present extended wear lenses based on hydrophilic polymeric materials has also provided a shifting and changing need for new and more effective means for cleaning such lense materials to maintain optical clarity, wearability and prevent the transfer of infectious agents into the eye.

Glass and the early polymer such as polymethylmethacrylate (PMMA) lenses could be readily cleaned by manual means using detergent because of their rigidity and hydrophobic character. Hydrophilic materials, particularly polypeptides and enzymes such as lysozyme, do not adhere significantly to these materials and are readily removed by cleaning with surfactants and detergents.

In all contact lense polymers now in use, except for the PMMA lenses, the lense surface is naturally hydrophilic or treated to make it hydrophilic. Proteinaceous materials absorb upon the hydrophilic lense surface during day-to-day wear. On all but purely PMMA lenses, the adsorption is so strong that even with lenses such as the rigid polysiloxane/methylmethacrylate copolymers, manual detergent cleaning methods do not adequately remove this accretion. Moreover, so-called hydrogel lenses, those materials prepared from hydroxyethylmethacrylate, hydroxyethylmethylmethacrylate, vinylpyrrolidone and glycerol-methacrylate monomers and methacrylic acid or acid esters, and which absorb a significant amount of water, i.e., 35–80 percent water, are so fragile that mechanically cleaning is not a practical way of removing soilants, particularly the strongly absorbed proteinaceous materials.

The only safe and effective means found to date for removing protein build-up is the use of enzymes, whose hydrolytic activity reduce the proteinaceous materials to small, water soluble subunits. Particularly useful are proteolytic enzymes or proteases, which hydrolyze amide bonds to break proteins down into amino acids and very small polypeptides. These protein fragments are generally water soluble and thus are easily solubilized by the surrounding aqueous environment. Enzymes with lipolytic and or mucolytic activity are also of use in discrete amounts with proteolytic enzymes for lense cleaning. U.S. Pat. No. 3,910,296 discloses the use of proteases for cleaning contact lenses. See also U.S. Pat. No. 4,285,738 which suggests the use of a solution containing a protease and a reducing agent to clean proteinaceous matter on lenses.

Another problem with gas permeable contact lenses, especially the hydrogel or high-water contact lenses made from HEMA, VP and GMA monomers, are concerns with disinfecting and maintaining the sterility of the lenses and lense storage solutions.

A number of methods have been devised for disinfecting lenses, including the use of high temperature, sterile saline solution washes and chemicals, antimicrobial agents and oxidation processes.

Heat has been effective to a substantial degree but as noted above, it has been suggested that thermal disinfection promotes discoloration of hydrophilic lenses.

Sterile saline solutions are not always sterile as certain microbes can live in a saline environment and spores are not totally inactivated by sterile saline solutions.

U.S. Pat. No. 4,614,549 suggests that hydrophilic contact lenses can be cleaned and disinfected in one step by immersing the lenses in a proteolytic enzyme saline solution and heating using a standard thermal disinfecting unit. See G.L. Feldman and W. R. Bailey, "Clinical Experiences With Chemical vs. Thermal Disinfection of Hydrophilic Lenses", Contact Lense Journal, Sep., 1974 at page 18. However, lenses are oftentimes found to become discolored after repeated periods of use followed by repeated enzymatic cleaning and thermal disinfection using such methodology.

It has also been found that contact lenses may be simultaneously oxidatively cleaned and disinfected by combining in one solution a peroxide for disinfecting and a peroxide-active enzyme for cleaning, particularly a peroxide-active proteolytic enzyme. See U.S. Pat. Re. 32,672 to Huth et al. and assigned to Allergan, Inc.

Pigment deposits are most common among soft lense wearers. Oxidizing agents such as perioxides are known to remove lense pigmentation and decolorize the lense, but unfortunately when the pigment is oxidized and made soluble, small voids remain in the lense matrix. The lense then has a sponge, porous layer at the site of pigment deposition. Peroxide bleaches may also damage the lense polymer, resulting in a lense that is not fit for reuse. See Kleist, FD, "Appearance and Nature of Hydrophilic Contact Lense Deposits—Part 1: Protein and Other Organic Deposits", International Contact Lense Clinic, May/Jun. 1979 at page 55.

It has also been reported in a clinical study that a mixture of the proteolytic enzyme subtilisin dissolved in 3% hydrogen peroxide is more effective than hydrogen peroxide alone in removing discoloration. See Patel, "Removal of Lens Discoloration", Am. J. Opto, Physiol. Op., Oct., 1987.

None of the above disclosures teaches or contemplates the use of compositions for simultaneously cleaning, decolorizing and thermally disinfecting contact lenses.

SUMMARY OF THE INVENTION

In one aspect, this invention relates to a non-oxidative method for simultaneously (a) cleaning contact lenses, (b) thermally disinfecting contact lenses, and (c) removing or preventing contact lense discoloration, particularly lenses having a hydrophilic surface. The method comprises contacting the lense with a solution comprising an effective amount of an enzyme and a reducing agent, and heating the solution containing the lense, for a time and at a temperature sufficient to remove substantially all contact lense discoloration and protein accretions and to disinfect the lense.

SPECIFIC EMBODIMENTS

The method of combining an enzyme and a reducing agent to effect decolorizing, thermal disinfecting and cleaning in one step can be applied to thermally stable proteases, and proteolytic, lipolytic and mucolytic enzymes, individually or in combination.

Enzymes may be derived from any plant or animal source, including microbial and mammalian sources. They may be neutral, acidic or alkaline enzymes.

A thermally stable protease or thermophilic enzymes denotes a protease that is stable and active at temperatures higher than 70° C. or even higher than 100° C. One such heat stable protease is thermolysin. Reference may be had to pages 642–650 of Perlmann et al., "Proteolytic Enzymes," Method in Enzymology, Volume XIX, Academic Press (1970).

A proteolytic enzyme will have in part or in total the capacity to hydrolyze peptide amide bonds. Such enzyme raw materials may also have some lipolytic and/or amylolytic activity associated with the proteolytic activity.

A preferred group of proteolytic enzymes are the serine proteases, particularly those derived from Bacillus and Streptomyces bacteria and Asperigillus molds. Within this grouping, the more preferred enzymes are the Bacillus derived alkaline proteases generically called subtilisin enzymes. Reference is made to Keay, L, Moser, PW and Wildi, BS, "Proteases of the Genus Bacillus. II Alkaline Proteases," Biotechnology and Bioengineering, Vol. XII, pp. 213–249 (1970) and Keay, L and Moser, PW, "Differentiation of Alkaline Proteases form Bacillus Species", Biochemical and Biophysical Research Comm., Vol. 34, No. 5, pp. 600–604 (1969). Metallo-proteases, those enzymes which contain a divalent metal ion such as calcium, magnesium or zinc bound to the protein, may also be used.

The subtilisin enzymes include two sub-classes, subtilisin A and subtilisin B. In the subtilisin A grouping are enzymes derived from such species as *B. subtilis, B. licheniformis* and *B. pumilis*. Organisms in this sub-class produce little or no neutral protease or amylase. The subtilisin B sub-class includes enzymes from such organisms as *B. subtilis, B. subtilis* var. amylosacchariticus, *B. amyloliquefaceins* and *B. subtilis* NRRL B3411. These organisms produce neutral proteases and amylases on a level about comparable to their alkaline protease production.

In addition other preferred enzymes are, for example, pancreatin, trypsin, collagenase, keratinase, carboxylase, aminopeptidase, elastase, and aspergillopeptidase A and B, pronase E (from *S. griseus*) and dispase (from *Bacillus polymyxa*).

Generally, the preferred enzymes are active proteolytic enzymes, with the most preferred being subtilisin A. Some proteolytic enzymes such as papain may also require an activating agent such as a thiol as well as a chelating agent such as EDTA. The amount of the thiol will be sufficient to provide the enzymatic activity as discussed below.

The identification, separation and purification of enzymes is an old art. Many identification and isolation techniques exist in the general scientific literature for the isolation of enzymes, including those enzymes having proteolytic and mixed proteolytic/amylolytic or proteolytic/lipolytic activity. The enzymes contemplated by this invention can be readily obtained by known techniques from plant, animal or microbial sources.

With the advent of recombinant DNA techniques, it is anticipated that new sources and types of stable proteolytic enzymes will become available. Such enzymes should be considered to fall within the scope of this invention so long as they meet the criteria for stability and activity set forth herein. See Japanese Laid Open Application No. J6 0030-685 for one example of the production of proteases by recombinant DNA from *Bacillus subtilis*.

An effective amount of enzyme is to be used in the practice of this invention. Such amount will be that amount which effects removal in a reasonable time of substantially all proteinaceous deposits from a lense due to normal wear. A reasonable time may be a few hours or less, depending in part upon the heating temperature and time of heating as discussed below. This standard is also stated with reference to contact lense wearers with a history of normal pattern of protein accretion.

The amount of enzyme required to make an effective cleaner will depend on several factors, including the inherent activity of the enzyme, the purity of the enzyme, the amount of proteinaceous matter deposited on the lenses, the desired heating period and temperature, and the type of lenses.

As a basic yardstick, the working solution should contain sufficient enzyme to provide between about 0.001 to 2 Anson units, per single lense treatment. Higher or lower amounts may be used. Enzyme concentrations lower than these stated here probably will serve to clean the lense if sufficient time and heat is provided but such time may be so long and such heat so high as to be practically not useful in a usual lense cleaning and disinfecting regimen. Solutions with higher activity should effect more rapid cleaning but may involve amounts of material which are too sizeable for practical cleaning purposes. The range of the optimally preferred subtilisin A enzyme is preferably from 0.01 to 0.1 Anson units, per single lens treatment.

In weight/volume terms, since enzyme preparations are seldom pure, it is expected that the enzyme source will be used in amounts between about 0.001 to 5% of the final working solution. The precise amount will vary with the purity of the enzyme and will need to be finally determined on a lot-by-lot basis. In weight to weight terms, the enzyme amount will range from 0.1% to 30%. The range of the optimally preferred subtilisin A enzyme is preferably from 0.3% to 1.5% by weight.

Enzyme activity is pH dependent. For any given enzyme, there will be a particular pH range in which that enzyme will function best. The determination of such range can readily be done by known techniques. It is preferred to manipulate the working solution to an optimum pH range for a given enzyme but such is not an absolute requirement. Generally, it is preferred that the enzyme be selected to have substantial activity at a pH between 6.5 and about 9.5 and even more preferably at between 6.9 to 7.9.

The reducing agent source is generally any non-toxic reducing agent, either dry or liquid, depending in part upon whether the delivery system is tablet or solution. Although thiols are preferred and N-acetylcysteine more preferred, reducing agent sources generally include SH (group)-containing water-soluble lower alcohols, organic carboxylic acids, organic amines and salts thereof, amino acids and di- or tripeptides, e.g. acetylcysteine, cysteine hydrochloride ethyl ester, glutathione, homocysteine, carbamoyl cysteine, cysteinylglycine, 2-mercaptopropionic acid, 2-mercaptopropionylglycine, 2-mercaptoethylamine hydrochloride, cysteine, beta mercaptoethanol, cysteine hydrochloride, dithiothreitol, dithioerythritol, sodium bisulfate, sodium metabisulfite, thio urea, and mixtures thereof.

Other reducing agents include sulfites, pyrosulfites and dithionites such as the alkali metal salts or alkaline earth metal salts of sulfurous acid, pyrosulfurous acid and dithinious acid, e.g. lithium, sodium, calcium and magnesium salts and mixtures thereof.

The amount of the reducing agent will depend upon the enzyme utilized, but will be sufficient so that the discolored lens will decolor upon thermal disinfection of the lense in the enzyme/reducing agent solution, as described in more detail below. In general, in weight to volume terms the reducing agent source will be used in amounts between 0.05% to 10% of the final working solution, with 0.5% to 1.5% preferred. In weight to weight terms, the general range will be 10% to 55%, with 10% to 24% preferred. With the most preferred reducing agent, N-acetylcysteine, used with from 0.7% to 1.0% pure subtilisin A, the range is preferably from 14% to 25% weight to weight.

It should be appreciated that without the reducing agent, a lense, heated in a saline solution containing the enzyme alone, may tend to discolor. This has been observed in practising U.S. Pat. No. 4,614,549 to Ogunbiyi which provides the foundation for Baush & Lomb's ThermaClean ® product.

On the other hand it should be appreciated that the methodology of the present invention exhibits a synergistic effect. That is, the enzymatic cleaning capability and thermal disinfecting capability are greater when the enzyme and reducing agent are used in combination with thermal disinfection, than when an enzyme solution alone is used in a cleaning regimen separate from thermal disinfection.

The enzyme and reducing agent may be employed in liquid or solid form usually in combination with additional components. Preferably, the enzyme and reducing agent are provided in solid form such as tablets or powders which are mixed with an aqueous saline solution prior to use.

Additional components may be added to or combined with the enzyme and reducing agent which do not substantially decrease the activity of the enzyme. For example, components such as effervescing agent, stabilizers, preservatives, buffering agents, chelating and/or sequestering agents, coloring agents, surfactants and the like can be employed. In addition, when tablets are employed, binders, lubricants, carriers, and other excipients normally used in producing tablets may be used.

It may be appropriate to add the buffering agents to these solutions to maintain the pH within a particular given range. Examples of suitable buffering agents which may be used include, but are not limited to, alkali metal salts such as potassium or sodium carbonates, acetates, borates, phosphates, citrates, hydroxides, and weak acids such as acetic and boric acids. Preferred buffering agents are alkali metal borates such as sodium or potassium borates. Additionally, other pH adjusting agents may be employed such as inorganic acids. For example, hydrogen chloride may be employed in concentrations suitable for ophthalmic uses. Generally, buffering agents are present in amounts from about 0.01 to about 2.5 percent by weight/volume.

Effervescing agents are typically employed when the enzyme is provided in solid form. Examples of suitable effervescing agents include, but are not limited to, tartaric or citric acid used in combination with a suitable alkali metal salt such as sodium carbonate.

Suitable surfactants can be either cationic, anionic, nonionic or amphoteric. Preferred surfactants are neutral or nonionic surfactants which may be present in amounts up to 5% (w/v). Examples of suitable surfactants include, but are not limited to, polyethylene glycol esters of fatty acids, polyoxypropylene ethers of $C_{12}$-$C_{18}$ alkanes and polyoxyethylene, polyoxypropylene block copolymers of ethylene diamine (i.e. polyoxamine). In this regard, the use of surfactants in a heat disinfecting regimen is known. See U.S. Pat. No. 4,104,187 to Sibley.

Examples of preferred chelating agents include ethylenediaminetetraacetic acid (EDTA) and it salts (disodium) which are normally employed in amounts from about 0.025 to about 2.0% (w/v). Other known chelating (or sequestering agents) such as certain polyvinyl alcohols can also be employed.

In tablets or powders, the same considerations may be in effect in the sense of adding in salts, buffers and stabilizers so that when the tablet is dissolved, the appropriate pH and tonic value will be present.

The binders and lubricants for tableting purposes and other excipients normally used for producing powders, tablets and the like, may be incorporated into such formulations.

To practice the invention, preferably the reducing agent and the enzyme in tablet form are dissolved in a liquid media solution, the lenses are contacted and immersed in this solution, and the immersed lenses heated. The preferred liquid media is standard buffered isotonic saline solutions, e.g., 0.9% (w/v) saline.

A variety of saline solutions can be used including those shown in Table 1 below.

TABLE 1

| Trade Name | Ingredients |
|---|---|
| Mirasol | NaCl, KCl, EDTA, sodium borate, sorbic acid, poloxamer 407, thimerosal 0.001%, buffered isotonic |
| Allergan Hydrocare preserved saline | Thimerosal 0.001%, NaCl, sequestering agent, boric acid, sodium borate, EDTA, NaOH to adjust pH, buffered isotonic |
| Unisol | NaCl, boric acid, sodium borate, buffered isotonic |

Although, isotonic 0.9% (w/v) saline is preferred, the saline solution can also be hypotonic or hypertonic. What is important is that the liquid media be such that the physical parameters of the lenses (e.g., size and shape) be maintained during operation of the methodology of the invention.

In the case where a tablet formulation and water or another non saline diluent is used, the tablet could further include sufficient salts, electrolytes, buffers, tonicity agents and preservatives so that the tablet could be dissolved in such water or other diluent, and then heated, without adverse effect upon the lense physical parameters.

The method of sequence of combining the components to make up the solution which contacts the lenses will vary with the physical characteristics of the components employed; but the order of addition is not critical to the practice of this invention. For example, the enzyme and reducing agent could be separately formulated as tablets or powders.

It is most convenient to formulate the enzyme, reducing agent and other dry components as a powder or tablet and to dissolve such material in a saline solution, then introduce the lenses into this solution. The lenses could already be in the saline solution when the enzyme (in aqueous form) is introduced. However practical considerations make the first method the preferred one.

There is no particularly preferred form for the manufacturing of these materials. The two essential components may be formulated as separate components in dry or aqueous form. They may be combined in a single tablet or powder or liquid or one may be in dry form while the other is manufactured as an aqueous solution.

After the lense is immersed in the saline solution having therein an effective amount of an enzyme and a reducing agent, the immersed lense is preferably heated to a temperature which will disinfect and allow cleaning and decolorizing in one step in the same solution. The lenses in solution should be heated for a time period and at a temperature so that the lenses are essentially free of microorganisms and can be safely used. In this regard, the FDA prescribes thermal disinfection requirements which are adequate for the present invention and which are known to skilled artisans.

Typically, the enzyme and reducing agent in a saline solution are placed in a lense case well, the lense immersed in the solution, the lense case closed, and the closed lense case placed in a heating mechanism.

Heating is preferably carried out by a cycle consisting of a heating phase and a cooling phase. The heating phase consists of gradually elevating the temperature of the solution from ambient to a maximum temperature of usually less than 100° C., and more specifically, from at least 30° C., and preferably about 80° to about 90° C. When the maximum temperature has been reached the temperature is maintained usually for not more than 20 minutes, and more often for about 5 to about 15 minutes. It should be noted that the maximum temperature is dependent in part upon the enzyme. For more thermally stable enzymes such as the arabus enzyme or genetically engineered thermally stable enzymes, the maximum temperature may increase with less denaturation and greater cleaning over a shorter time period.

Although the precise mechanism for cleaning reaction remains uncertain, the activity of the enzyme, for example, and the denaturing and removing protein from lense surfaces, is believed to be enhanced as the temperature rises. Likewise, when the maximum temperature has been reached during the heating phase and maintained for about 10 minutes, the enzyme is automatically inactivated terminating the cleaning process while simultaneously disinfecting the lenses. For example, for subtilisin A, in a saline solution having a pH ranging from 7.42 to 8.89 and an osmolality ranging from 465 mosm/kg to 517 mosm/kg, the enzyme remains active up to 60° C., with the total deactivation of the enzyme at 80° C.

At the conclusion of the heating phase, the cooling phase commences whereby the cleaned and disinfected lenses and the inactive cleaning solution are allowed to cool to ambient temperature. The lenses are then ready for reinserting onto the eyes.

The process is most conveniently conducted with any of the well known commercially available contact lense heat disinfecting units. Such heat disinfecting units, in most instances, can be adapted to the single step process. They have temperature profiles which typically include heating up to 80° C. which temperature is maintained for approximately 10 minutes; the entire cycle taking about 60 minutes. Temperature profiles of heat units can be modified depending on the type of lense and enzyme, where for instance, extended wear-type contacted lenses may be treated to even more abbreviated cleaning, disinfecting and decolorizing cycles and at lower temperature ranges to minimize the potential for physical damage.

The amount of decolorization is proportional to the length of treatment. Depending upon the degree of discoloration, it may be necessary to repeat the process steps and the thermal heating unit cycle more than once.

Other energy input may be employed to potentiate the solution's cleaning, decolorizing and disinfecting effect. For example, ultrasonic devices are known to potentiate the speed at which proteases work in such circumstances as well as the cleaning and disinfecting rates.

The practice of this invention is not to be limited temperature-wise except by those temperatures extremes which would substantially inactivate the proteolytic capability of the enzymes employed before the cleaning and decolorizing function is complete, and by temperatures which would not disinfect the lense over a reasonable (say a few hours) period of time. Enzymatic activity is a function of temperature, some enzymes being considerably more labile than others to temperature extremes, particularly temperature increases. Other enzymes are heat stable and remain significantly active at temperatures of 70° C. or higher.

The following examples are set out to illustrate, but not limit, the scope of this invention.

EXAMPLE 1

| Ingredient | Percentage (w/w) |
| --- | --- |
| Subtilisin A | 0.30% |
| N-acetylcysteine | 22.49% |
| Sodium Carbonate, anhydrous | 38.98% |
| Sorbitol, FG instant | 29.99% |
| Polyethylene glycol (PEG) 3350 | 3.00% |
| Tartaric Acid | 5.24% |

EXAMPLE 2

| Ingredient | Percentage (w/w) |
| --- | --- |
| Subtilisin A | 0.84% |
| N-acetylcysteine | 25.21% |
| Sodium Carbonate, anhydrous | 20.17% |
| Sorbitol, FG instant | 50.42% |
| PEG 3350 | 3.36% |

EXAMPLE 3

| Ingredient | Percentage (w/w) |
| --- | --- |
| Subtilisin A | 0.917% |
| N-acetylcysteine | 18.349% |
| Sodium carbonate, anhydrous | 22.018% |
| Sorbitol, FG instant | 55.046% |
| PEG 3350 | 3.670% |

EXAMPLE 4

| Ingredient | Percentage (w/w) |
| --- | --- |
| Subtilisin A | 0.735% |
| N-acetylcysteine | 18.382% |
| Sodium Carbonate, anhydrous | 22.059% |
| Sorbitol, FG instant | 55.147% |
| PEG 3350 | 3.676% |

EXAMPLE 5

| Ingredient | Percentage (w/w) |
| --- | --- |
| Subtilisin A | 1.099% |
| N-acetylcysteine | 18.315% |
| Sodium Carbonate, anhydrous | 21.978% |
| Sorbitol, FG instant | 54.945% |
| PEG 3350 | 3.663% |

EXAMPLE 6

| Ingredient | Percentage (w/w) |
| --- | --- |
| Subtilisin A | 1.042% |
| N-acetylcysteine | 17.361% |
| Sodium Carbonate, anhydrous | 26.042% |
| Sorbitol, FG instant | 52.083% |
| PEG 3350 | 3.472% |

EXAMPLE 7

| Ingredient | Percentage (w/w) |
| --- | --- |
| Subtilisin A | 0.901% |
| N-acetylcysteine | 14.414% |
| Sodium Carbonate, anhydrous | 30.631% |
| Sorbitol, FG Instant | 50.45% |
| PEG 3350 | 3.604% |

The subtilisin A was obtained from Novo Industries of Copenhagen Denmark.

For a 60 milligram tablet formulated according to Examples 1-7, about 1 to 3 milliliters of standard buffered isotonic saline solution is preferred as the typical lense case will accommodate such a volume. The saline volume range is generally dependant upon the volume of the lense well of the thermal disinfection unit. If less than 0.5 milliliters of saline solution is used, the lense may not be totally immersed. On the other hand, for a 60 milligram tablet, 10 milliliters of saline solution can be used if the lense well is large enough.

The practice of the process of the present invention removes protein accretions, disinfects and substantially decolorizes the lenses. Generally, discolored lenses range from brown, to yellow brown, to yellow, to decreasing shades of yellow, to clear. The decolorization can be seen visually by comparing the treated and untreated lenses against a well-lit white background via the unaided eye, or via photomicroscopy or via ultraviolet and visible spectroscopy.

The decolorization methodology can be used in connection with new lenses to prevent discolorization, or with worn lenses to eliminate existing discolorization. In addition, lenses which have become discolored due to use of other enzymatic cleaners and heat disinfection, e.g. via use of Bauch & Lomb's Thermaclean ®, can be decolorized using the methodology of the present invention.

It should be appreciated to those of skill in the art that the present invention is not limited to the specific examples set forth above, and that many modifications and variations are within the scope of the present invention.

What is claimed is:

1. A method for removing yellow contact lense discoloration from a contact lense which method comprises contacting the lense with a solution comprised of a reducing agent and an enzyme and then heating the lense above ambient temperature for a time and at a temperature so as to remove substantially all of the yellow lense discoloration.

2. The method of claim 1 wherein the enzyme is a proteolytic enzyme and the reducing agent is a thiol.

3. The method of claim 1 wherein the reducing agent and the enzyme are combined in powder or tablet form.

4. The method of claim 1 wherein the reducing agent and the enzyme are dissolved in an aqueous solution.

5. The method of claim 1 wherein the enzyme is present in an amount between 0.001 and 2 Anson units.

6. The method of claim 1 wherein the solution containing the lense is heated to a temperature in a range from at least 30° C. to about 90° C.

7. The method of claim 1 wherein the solution is non-oxidative.

8. The method of claim 1, wherein the reducing agent is selected from the group consisting of cysteine hydrochloride, N-acetylcysteine, beta-mercaptoethanol, dithiothreitol, dithioerythritol, sodium bisulfate, sodium metabisulfite, thio urea, and mixtures thereof.

9. The method of claim 1 wherein the reducing agent is a thiol.

10. The method of claim 9 wherein the thiol is N-acetylcysteine.

11. The method of claim 10 wherein the reducing agent is N-acetylcysteine and the enzyme is subtilisin A.

12. The method of claim 1 wherein the enzyme is a proteolytic enzyme.

13. The method according to claim 12 wherein the proteolytic enzyme is a subtilisin enzyme.

14. The method of claim 13 wherein the subtilisin enzyme is subtilisin A.

15. The method of claim 1 wherein the amount of the reducing agent ranges from 0.05% to 10% (w/v).

16. The method of claim 1 wherein the amount of the reducing agent ranges from 0.5% to 1.5% (w/v).

17. The method of claim 1 wherein the amount of the enzyme ranges from 0.001 to 2 Anson units.

18. The method of claim 1 wherein the reducing agent is a thiol and the amount of the thiol ranges from 0.5% to 10% (w/v).

19. The method of claim 1 wherein the enzyme is a proteolytic enzyme and the amount of the proteolytic enzyme ranges from 0.001 to 2 Anson units.

20. The method of claim 1 wherein there is present from 0.05 to 10% (w/v) of a thiol and from 0.001 to 2 Anson units of proteolytic enzyme.

21. The method of claim 11 wherein there is present from 0.5 to 1.5% (w/v) of N-acetylcysteine and from 0.01 to 0.1 Anson units of subtilisin A.

22. A method for simultaneously cleaning, disinfecting and removing yellow discoloration from a contact lense, the method comprising the steps of:
 a. immersing the lense in an aqueous solution including an effective amount of a thiol and an enzyme; and
 b. heating the solution containing the immersed lense above ambient temperature for a time and at a temperature sufficient to remove substantially all yellow lense discoloration and contact lense protein accretions and to disinfect the lense.

23. The method of claim 22 wherein the enzyme and thiol are in a powder or tablet form and are dissolved in an aqueous solution.

24. The method of claim 22 wherein the enzyme is present in an amount between 0.001 and 2 Anson units.

25. The method of claim 22 wherein the enzyme is subtilisin a and is present in an amount between 0.001 and 5% by weight.

26. The method of claim 22 wherein the thiol is N-acetylcysteine and is present in an amount between 0.05% and 10% by weight.

27. The method of claim 22 wherein the solution comprises 14% to 25% N-acetylcysteine and 0.7 to 1.0% subtilisin A by weight.

28. The method of claim 27 wherein the thiol and enzyme are dissolved in from 1 to 3 ml of an aqueous solution.

29. The method of claim 22 wherein the enzyme is subtilisin A and is present in an amount between 0.01 and 0.1 Anson units.

30. The method of claim 1 wherein the contact lense has a hydrophilic surface.

31. The method of claim 1 wherein the enzyme is a thermophilic enzyme.

32. The method of claim 1 wherein the solution containing the lense is heated to a maximum temperature in a range of approximately 80° C. to approximately 90° C.

33. The method of claim 1 wherein the solution containing the lense is heated from ambient temperature to a temperature of at least 30° C.

34. The method of claim 22 wherein the solution containing the immersed lense is heated to a maximum temperature in a range of approximately 80° C. to approximately 90° C.

35. The method of claim 22 wherein the solution containing the immersed lense is heated from ambient temperature to a temperature of at least 30° C.

* * * * *

UNITED STATES PATENT AND TRADEMARK OFFICE
CERTIFICATE OF CORRECTION

PATENT NO. : 5,209,783
DATED : May 11, 1993
INVENTOR(S) : Stanley W. Huth, Sam W. Lam, Abraham M. Espiritu It is certified that error appears in the above-identified patent and that said Letters Patent is hereby corrected as shown below:

Col. 1, Line 47
Contact Lens Forum, [Sept.], September 1984

Col. 1, Line 61
Glass and the early [polymer] polymers

Col. 2, Line 56
Contact Lens Journal, [Sept.] September

Col. 3, Line 4
The lense then has a [sponge] spongy

Col. 3, Line 16
Physiol. Op., [Oct.], October

Col. 5, Line 53
with 10% to [24]% 25 preferred.

Signed and Sealed this

Twenty-second Day of February, 1994

Attest:

BRUCE LEHMAN

Attesting Officer      Commissioner of Patents and Trademarks